United States Patent
McKenna

(10) Patent No.: US 8,791,412 B2
(45) Date of Patent: Jul. 29, 2014

(54) OPTICAL SYSTEM CALIBRATION VERIFICATION

(75) Inventor: Gilbert W. McKenna, Revere, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 13/818,705

(22) PCT Filed: Sep. 1, 2010

(86) PCT No.: PCT/US2010/047501
§ 371 (c)(1),
(2), (4) Date: Feb. 25, 2013

(87) PCT Pub. No.: WO2012/030334
PCT Pub. Date: Mar. 8, 2012

(65) Prior Publication Data
US 2013/0153786 A1   Jun. 20, 2013

(51) Int. Cl.
*G01N 1/10* (2006.01)

(52) U.S. Cl.
USPC ............ 250/305; 250/306; 250/307; 250/309

(58) Field of Classification Search
USPC .................................. 250/305, 306, 307, 309
See application file for complete search history.

(56) References Cited

U.S. PATENT DOCUMENTS

| | | | | |
|---|---|---|---|---|
| 3,973,129 A * | 8/1976 | Blumberg et al. | ......... | 250/461.2 |
| 6,094,274 A * | 7/2000 | Yokoi | ........................... | 356/417 |
| 6,471,916 B1 * | 10/2002 | Noblett | ...................... | 422/82.08 |
| 6,940,069 B2 * | 9/2005 | Hiroi et al. | ...................... | 850/10 |
| 7,329,502 B2 * | 2/2008 | Staudt et al. | ................. | 435/7.23 |
| 7,981,610 B2 * | 7/2011 | Staudt et al. | ................. | 435/6.14 |
| 8,427,637 B2 * | 4/2013 | Gao | ............................. | 356/246 |
| 8,492,138 B2 * | 7/2013 | Boege et al. | ............... | 435/288.7 |
| 2003/0203416 A1 * | 10/2003 | Staudt et al. | ................. | 435/7.23 |
| 2012/0187021 A1 * | 7/2012 | McKenna | ...................... | 206/569 |
| 2013/0087206 A1 * | 4/2013 | Mckenna et al. | ................. | 137/1 |
| 2013/0115607 A1 * | 5/2013 | Nielsen et al. | ............... | 435/6.12 |
| 2013/0153786 A1 * | 6/2013 | McKenna | ................ | 250/453.11 |

OTHER PUBLICATIONS

International search report for PCT/US2010/047501 published as WO 2012/030334 A1, May 23, 2011.

* cited by examiner

*Primary Examiner* — David A Vanore
(74) *Attorney, Agent, or Firm* — Driggs, Hogg, Daugherty & Del Zoppo, Co., LPA

(57) ABSTRACT

A sample processing apparatus (102) includes a reference carrier region (106) that supports a reference carrier (108), which includes one or more reference substances that emit radiation with unique and known spectral characteristics in response to being irradiated with radiation having a wavelength in a predetermined range of interest. The sample processing apparatus further includes a carrier receiving region (110) configured to alternatively receive a sample carrier (104) or the reference carrier for processing by the apparatus. The sample processing apparatus further includes an optical component (114, 116, 118) that emits radiation, having a wavelength in a predetermined range of interest, that irradiates the carrier in the carrier receiving region, and that detects the radiation emitted from the carrier. The apparatus moves the reference carrier from the reference carrier region to the carrier receiving region for processing by the apparatus.

24 Claims, 5 Drawing Sheets

OPTICAL SYSTEM CALIBRATION VERIFICATION

RELATED APPLICATION

This application is a national filing of PCT application Serial No. PCT/US2010/047501, filed Sep. 1, 2010, published as WO 2012/030334 A1 on Mar. 8, 2012.

TECHNICAL FIELD

The following generally relates to optical systems and finds particular application to verifying calibration and/or functionally of an optical based device such as a DNA sequencer and/or other optical system.

BACKGROUND

A DNA sequencer is an apparatus that determine the order (or sequence) of the nucleotide bases (adenine, guanine, cytosine, and thymine) in a sample of DNA. With one sequencing technique, DNA is extracted from a bio-sample and purified. The purified DNA is lysed, and fragments thereof are replicated through polymerase chain reaction (PCR). A reference material containing synthesized fragments of known fragment sizes is added to the sample containing the replicated fragments. The DNA and reference fragments are labeled with target specific fluorescent dyes, each with a known and unique spectral response, and the labeled fragments are separated through electrophoresis. An optical component transmits radiation, having a wavelength within a predetermined wavelength range, which irradiates and excites the dyes of the separated fragments, receives characteristic fluorescent radiation emitted by the dyes in response to being irradiated, and generates electrical signals indicative of the received characteristic fluorescent radiations. The signal corresponding to the DNA under evaluation is used to sequence the DNA fragments by nucleotide base based on the spectral characteristics.

The signal corresponding to the reference material may be used to verify calibration and/or functionality of the sequencer. Unfortunately, the DNA and reference material are concurrently processed. As a consequence, if the signal corresponding to the reference material indicates that the sequencer is out of calibration or not functioning properly, the sequencer results are discarded, the sample is disposed, and another sample has to be obtained, prepared, and processed after the sequencer is re-calibrated and its functionality is verified. However, even after re-calibration and verification, external forces, temperature, vibrations, shock, and/or other influences, for example, from the time of calibration to the time of use, may throw the calibrated and verified system out of calibration, and this may not be detected until after the concurrent processing of another DNA sample and reference material. As discussed above, this may lead to discarding the results, disposing of the sample, re-calibration of the sequencer, and processing of another sample, if the signal corresponding to the reference material indicates that the sequencer is out of calibration or not functioning properly.

SUMMARY

Aspects of the application address the above matters, and others.

In one aspect, a sample processing apparatus includes a reference carrier region that supports a reference carrier, which includes one or more reference substances that emit radiation with unique and known spectral characteristics in response to being irradiated with radiation having a wavelength in a predetermined range of interest. The sample processing apparatus further includes a carrier receiving region configured to alternatively receive a sample carrier or the reference carrier for processing by the apparatus. The sample processing apparatus further includes an optical component that emits radiation, having a wavelength in a predetermined range of interest, that irradiates the carrier in the carrier receiving region, and that detects the radiation emitted from the carrier. The apparatus moves the reference carrier from the reference carrier region to the carrier receiving region for processing by the apparatus.

In another aspect, an method includes moving a reference carrier supported by a sample processing apparatus into a carrier receiving region of the apparatus for processing of one or more reference substances of the reference carrier by the apparatus when a sample carrier is not in the carrier receiving region, wherein the apparatus automatically moves the reference carrier into the carrier receiving region. The method further includes processing, via a processing station of the apparatus, the one or more substances carried by the reference carrier in the carrier receiving region. The method further includes generating a signal indicating whether the apparatus is calibrated based on a result of the processing.

In another aspect, a sample processing apparatus includes a component that automatically moves a reference carrier of the sample processing apparatus into a carrier receiving region of the sample processing apparatus for processing by the sample processing apparatus. Processing the reference carrier includes generating a signal indicative of whether the sample processing apparatus is calibrated based on optical characteristics of one or more reference substances carried by the reference carrier.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
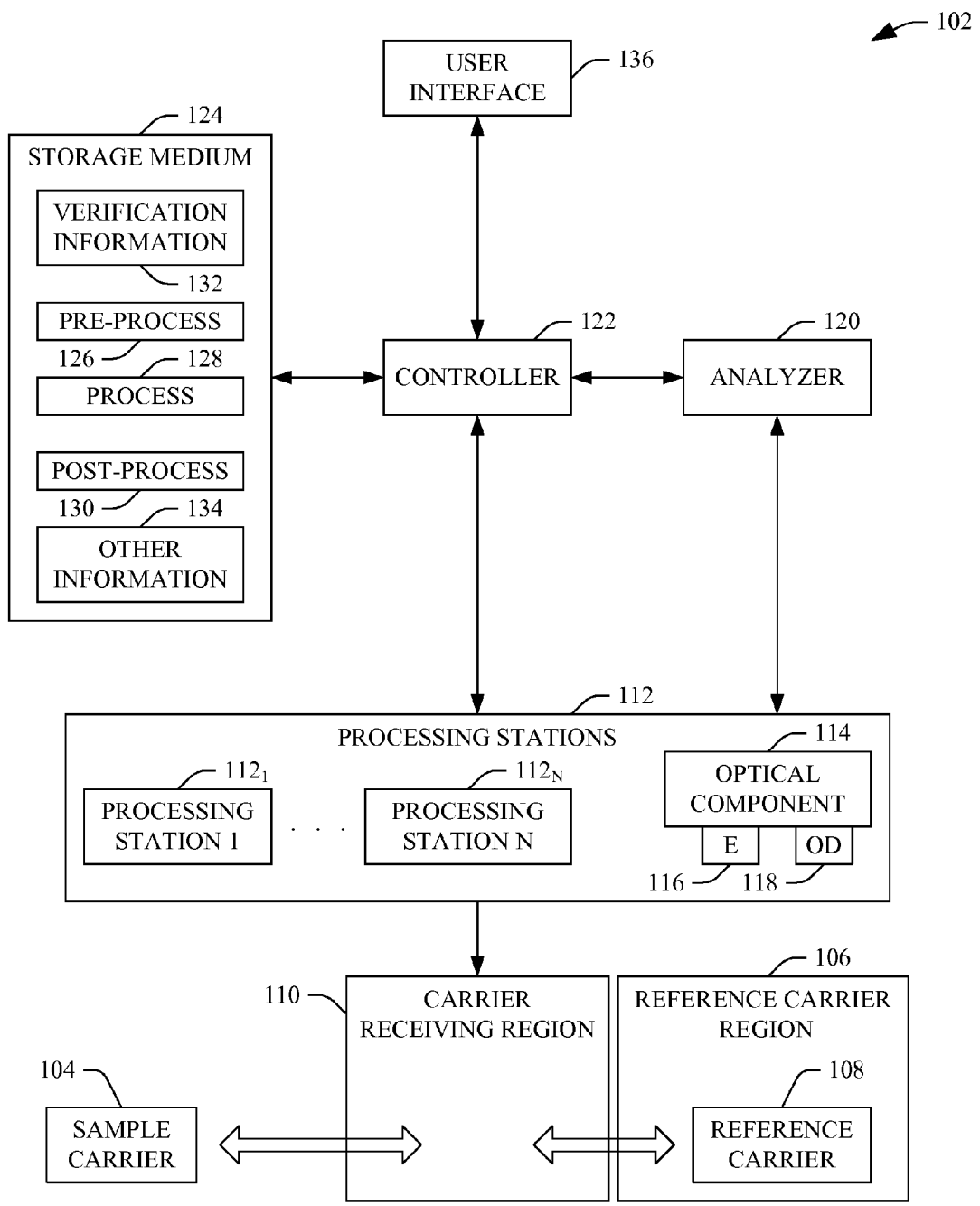
FIG. 1 illustrates an example sample processing apparatus with a self deployable reference carrier that can be used to verify apparatus calibration and/or functionality.

FIG. 1 illustrates a sample processing apparatus 102 for processing one or more samples carried by a sample carrier 104. The illustrated sample processing apparatus 102 is configured to process at least one or more samples of DNA, such processing including, but not limited to sequencing DNA nucleotide bases (adenine, guanine, cytosine, and thymine) of DNA in a sample.

An example of a suitable sample carrier 104 includes, but is not limited to, a biochip, a lab-on-a-chip, and/or other sample carriers carrying a bio or non-bio sample. Such a sample carrier 104 may include one or more micro-channels or lanes for carrying and moving one or more different samples through multiple different processing regions of the sample carrier 104, for example, during concurrent or parallel processing of the samples thereon. Micro-fluidics and/or other technology can be used to move a sample from processing region to processing region, a reagent to a processing region, etc. The illustrated sample carrier 104 carries at least one sample that includes DNA.

The sample processing apparatus 102 includes a reference carrier region 106 that supports a reference carrier 108, which, in this embodiment, includes one or more reference substances (e.g., electroflorecent materials), each having unique and known spectral response to a particular wavelength range of interest of the electromagnetic spectrum. The reference carrier region 106 is configured to carry the reference carrier 108 at least when a sample carrier 104 is loaded in the apparatus 102. As described in greater detail below, various approaches, including internally deployable approaches, can be used to move the reference carrier 108 into and out of the reference carrier region 106 for positioning the reference carrier 108 for processing by the sample processing apparatus 102.

The reference carrier 108 can be processed by the apparatus 102 before and/or after processing of samples of the sample carrier 104. In one instance, this allows for verifying calibration and/or functionality of the sample processing apparatus 102 during a warm up or pre-sample processing phase of the sample processing apparatus 102. This may facilitate mitigating processing samples carried by the sample carrier 104 and finding out after such processing that the sample processing apparatus 102 is not calibrated and/or is functioning improperly, and having to discard the results and obtain and process another sample after re-calibration.

The sample processing apparatus 102 also includes a carrier receiving region 110 that is configured to alternatively receive the sample carrier 104 or the reference carrier 108. The carrier receiving region 110 supports a loaded carrier 104 or 108 for processing by the sample processing apparatus 102. The carrier receiving region 110 can carry the reference carrier 108 at least when a sample carrier 104 is not loaded in the apparatus 102, including in a laboratory, during transportation, and/or at a site of deployment or use of the apparatus to process samples. In the illustrated embodiment, neither the sample carrier 104 nor the reference carrier 108 is loaded in the carrier receiving region 110. In another non-limiting embodiment, the reference carrier 108 is always loaded into the carrier receiving region 110 when the sample carrier 104 is not in the carrier receiving region 110. In yet another embodiment, another carrier can be loaded into the carrier receiving region 110.

The sample processing apparatus 102 further includes one or more processing stations 112$_1$, ..., 112$_N$ (wherein N is an integer equal to or greater than one), collectively referred to herein as processing stations 112, that process samples of the loaded sample carrier 104 or the loaded reference carrier 108. The illustrated processing stations 112 are configured to carry out at least the following on samples carried by the sample carrier 104 when the sample carrier 104 is loaded in the carrier receiving region 110: extraction/purification of DNA from the sample, replication/amplification and labeling of the fragments (e.g., through PCR), and separation of the fragments (e.g., through electrophoresis). Generally, labeling includes labeling the DNA and any reference material fragments with target specific (nucleotide base and reference material) fluorescent dyes that have unique and known spectral characteristic (e.g., wavelengths of fluorescence and emission) in response to the wavelength range of interest.

The processing stations 112 also include an optical component 114 with an emitter (E) 116 and an optical detector (OD) 118. The emitter 116 is configured to emit electromagnetic radiation in the wavelength range of interest that irradiates the carrier (104 or 108) loaded in an examination region of the carrier receiving region 110. The optical detector 118 detects electromagnetic radiation emitted by the labels in the sample (where a sample carrier 104 is loaded in carrier receiving region 110) or the reference substances (where a reference carrier 108 is loaded in carrier receiving region 110), in response to being irradiated by the emitted radiation. The optical component 114 generates a signal indicative thereof the received information.

The sample processing apparatus 102 further includes an analyzer 120. The analyzer 120, when the sample processing apparatus 102 is used to process the sample carrier 104, sequences the DNA fragments in the processed sample based on the signal from the optical component 114. In this instance, the analyzer 120 may also verify calibration and/or functionality of the apparatus via the reference material of the sample carrier 104 based on the signal from the optical component 114. When the sample processing apparatus 102 is used to process the reference carrier 108, the analyzer 120 verifies calibration and/or functionality of the apparatus and/or facilitates auto calibration thereof via the references substances of the reference carrier 108 based on the signal from the optical component 114.

The sample processing apparatus 102 further includes a controller 122 that controls the processing stations 112 and/or the analyzer 120. In one instance, this may include controlling the processing stations 112 and/or the analyzer 120 based on one or more instructions in a storage medium 124 such as pre-(sample) processing instructions 126, (sample) processing instructions 128, and/or post-(sample) processing instructions 130. Generally, pre-(sample) processing instructions 126 relate to instructions utilized prior to processing the sample carrier 104, for example, during a warm up sequence, (sample) processing instructions 128 relate to instructions utilized for processing the sample carrier 104, and post-(sample) processing instructions 130 relate to instructions utilized after processing the sample carrier 104.

The storage medium 124 may also stores verification information 132 for verifying calibration and/or functionality of the sample processing apparatus 102. These instructions may be utilized by the controller 122 and/or the analyzer 120. For example, the analyzer 120 can compare the verification information with measured information to facilitate verifying the apparatus is calibrated and functioning. The storage medium 124 may also store other information 134 such as DNA sequencing results, information about the apparatus 102 (e.g., a unique identification (UID), model number, etc.), results of a calibration check, a date and/or time of the last verification, and/or other information.

The sample processing apparatus 102 further includes a user interface 136. The user interface 136 includes various input devices (e.g., keys, buttons, knobs, a microphone, etc.) and/or output devices (e.g., a display, a speaker, etc.). Such devices allow a user to interact with the sample processing apparatus 102. For example, the user interface 136 may allow a user to turn the apparatus 102 on and off, activate sequencing, pause or terminate sequencing, run a calibration check, etc. The controller 122 can also present visual and/or audible notifications via the output devices. For example, the controller 122 can present a notification indicating that the processing apparatus 102 is not calibrated and/or failed verification, the processing apparatus 102 is ready to process the sample carrier 104, the sample carrier 104 has been processed and can be removed from the carrier receiving region 110, etc.

It is to be appreciated that the sample processing apparatus 102 may be configured to be a portable apparatus that can be readily carried by an operator or moved via wheels or the like. In another embodiment, the sample processing apparatus 102 is configured to be a stationary apparatus mounted to or placed on a table, the floor, etc. in a laboratory, office, or the like. In such a configuration, the sample processing apparatus 102 may be configured to remain at a particular location and process samples.

Figure 2:
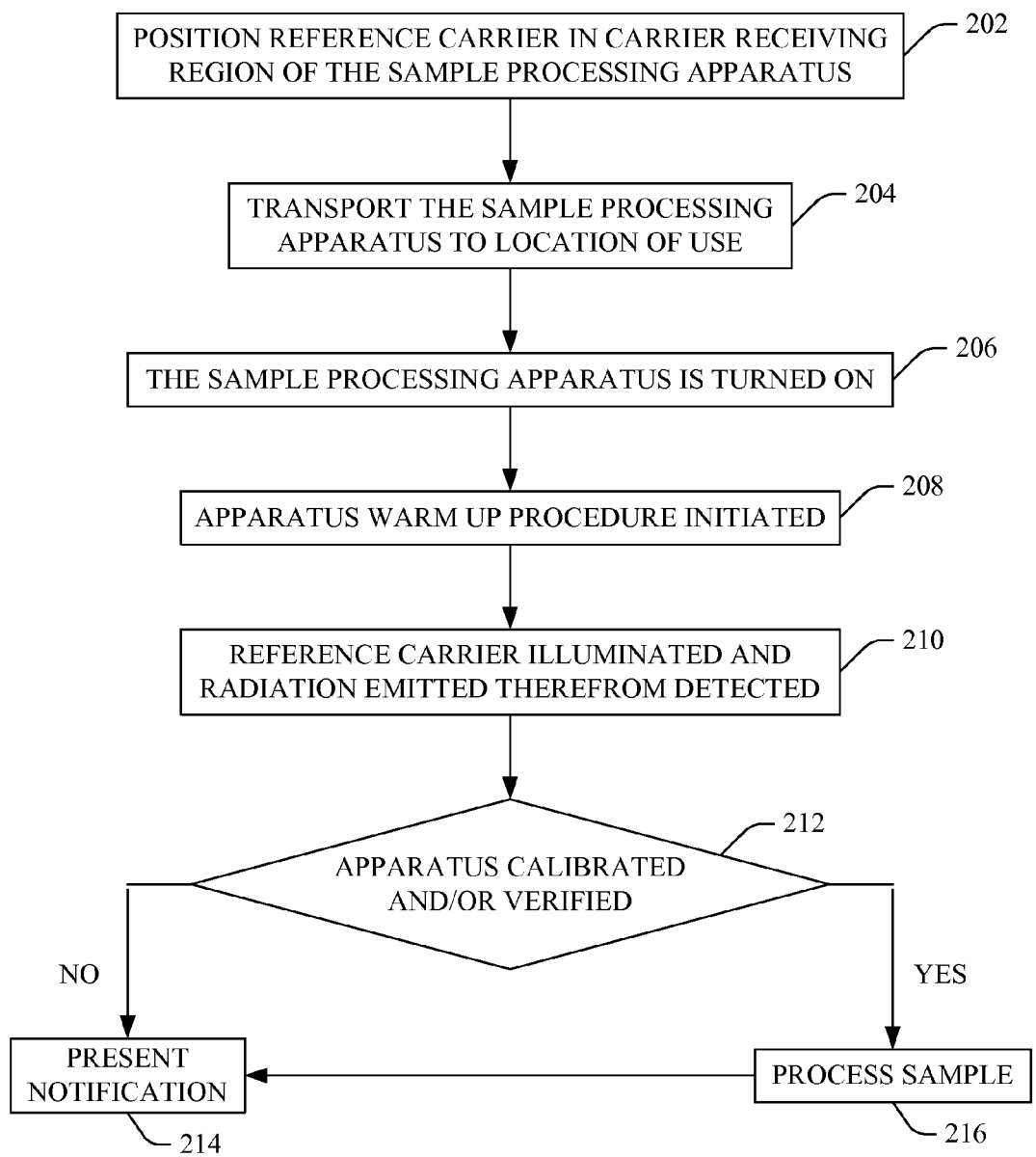
FIG. 2 illustrates an example method for verifying sample processing apparatus calibration and/or functionality.

FIG. 2 illustrates an example method in connection with employing the sample processing apparatus 102.

At 202, the reference carrier 108 is positioned in the carrier receiving region 110, if not already in the carrier receiving region 110. For example, the reference carrier 108 may automatically be loaded in the carrier receiving region 110, for instance, automatically in response to the sample carrier 104 being unloaded from the carrier receiving region 110. Alternatively, the reference carrier 108 is manually or semi-automatically loaded in the carrier receiving region 110.

At 204, the sample processing apparatus 102 is transported to the location where it will be employed such as the location where the sample is obtained, if not already there. In one instance, this may include at least bringing the sample processing apparatus 102 to the location via authorized personnel carrying the sample processing apparatus 102, an automobile, a cart with wheels, etc. In another embodiment, this act is omitted, for example, where the sample processing apparatus 102 is a laboratory mounted apparatus.

At 206, the sample processing apparatus 102 is turned on, if not already on. This may be achieved via the user interface 136.

At 208, the controller 122 executes pre sample processing warm up instructions 126.

At 210, the optical component 114 illuminates the reference carrier 108 with radiation of the predetermined wavelength range of interest and detects the radiation emitted from the reference substances in response to the illuminating radiation.

At 212, the processing apparatus 102 determines whether the processing apparatus 102 is calibrated and/or functioning properly based on the detected radiation and the verification information 132. For example, the processing apparatus 102 may compare spectral characteristics of the detected radiation with predetermined spectral characteristics for the reference substance and generate a signal indicating whether the detected radiation leads to the correct result.

At 214, if not, then the controller 122 presents a notification indicating the processing apparatus 102 is not calibrated and/or failed verification. This may also transition the processing apparatus 102 into a state in which it will not begin processing a loaded sample carrier 104, unless overridden by authorized personnel and/or subsequent pre-sample processing that indicates the processing apparatus 102 is calibrated and verified. This may additionally or alternatively transition the processing apparatus 102 into an auto-calibration state.

At 216, if so, then the apparatus 102 can be employed to process one or more samples of the sample carrier 104 as described herein. The controller 122 may present a notification indicating that processing has begun, is currently running, and/or has finished.

It is to be appreciated that one or more of acts 208-214 can be performed more than once. For example, in one embodiment, the apparatus 102 is configured so that if the sample is not processed within a predetermined time duration after verification, the controller 122 re-checks calibration and/or functionality again beginning with act 210. This can be done automatically or semi-automatically (e.g., a notification is presented, and a user initiates or rejects the re-check).

In another embodiment, the re-check is performed after processing a sample carrier 104 and/or between processing sample carriers 104. In another embodiment, the user initiates the re-check on-demand via the user interface 136. In yet another embodiment, turning the apparatus 102 off and back on re-starts the warm up procedure (act 208).

It is also to be appreciated that acts 202-214 can be performed in instances in which there is no sample carrier 104 to process, one or more times before and/or after processing the sample carrier 104, during preventative or corrective maintenance, etc.

The reference carrier 108 can also be used by the apparatus 102 to allow the optical component 114 to auto calibrate. By way of example, with the known response of the substances of the reference carrier 108, adjustments to the transmitter 116 and/or receiver 118 can be automated via the controller 122. Auto-calibration may be invoked after act 212 and/or otherwise.

By using one or more of pre, during, and/or post sample processing verification checks, the calibration and/or functionality of the processing apparatus 102 may be checked before, during, and/or after processing a sample on the sample carrier 104, which may facilitate validating (or invalidating, depending on the conclusion from the check) the results of the DNA sequencing. In this way the likelihood of the apparatus 102 not working correctly to evaluate a valuable unknown sample may be drastically reduced. Furthermore, if the measurement shows that the apparatus 102 is functioning, but just marginally, the apparatus 102 can be scheduled for maintenance before it actually fails and gives a false or otherwise incorrect reading of an unknown sample.

As noted herein, various approaches can be used to move the reference carrier 108 into and out of carrier receiving region 110 for processing by the sample processing apparatus 102. FIGS. 3-5 below illustrates several non-limiting examples.

Figure 3A:
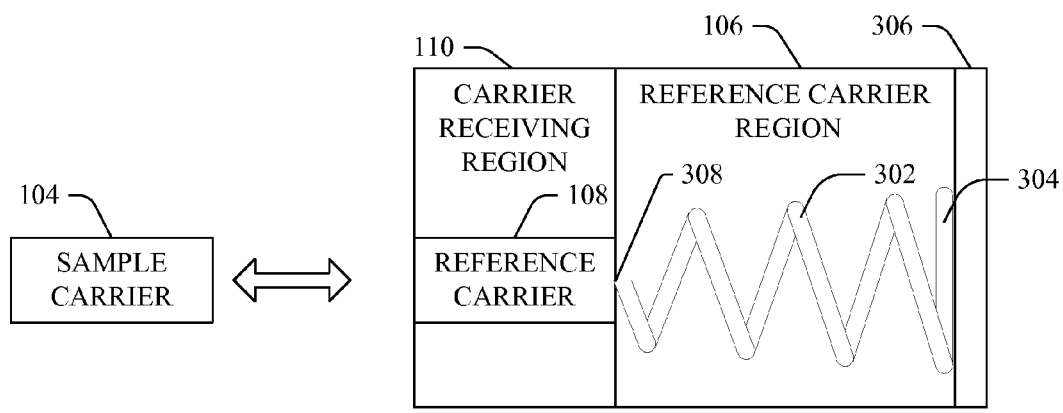
FIGS. 3-5 illustrate non-limiting examples of approaches for moving the reference carrier into and out of a carrier processing region of a sample processing apparatus for processing.
Figure 3B:
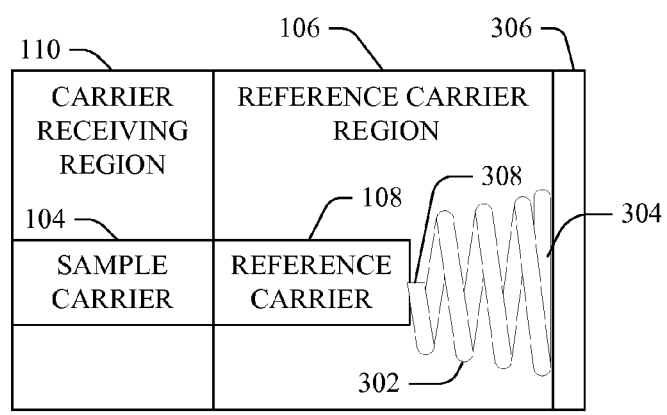

FIGS. 3A and 3B illustrate an embodiment in which an elastic component 302 (e.g., such as, but not limited to, a compression spring, as illustrated) is utilized to facilitate moving the reference carrier 108 in and out of the reference carrier region 106 for processing.

In both figures, a first end region 304 of the elastic component 302 is affixed to a stationary portion 306 of the apparatus 102 such as a stationary region of the reference carrier region 106, and a second opposing end region 308 of the elastic component 302 is affixed to the reference carrier 108.

FIG. 3A shows an instance in which the sample carrier 104 is outside of or not installed in the carrier receiving region 110. In this instance, the elastic component 302 is in a non-compression state, positioning the reference carrier 108, which is free to move, in the carrier receiving region 110. In this position, the reference carrier 108 can be processed by the apparatus 102 to verify calibration and/or functionality.

FIG. 3B shows an instance, in which the sample carrier 104 has been installed in the carrier receiving region 110. In this instance, the sample carrier 104 physically contacts the elastic component 302 and urges the elastic component 302 towards stationary portion 306, compressing the elastic component 302. This can be achieved as the user installs the sample carrier 104 in the carrier receiving region 110. In this position, the sample carrier 104 can be processed by the apparatus 102.

Removing the sample carrier 104 allows the elastic component 302 to return to the non-compression state, which returns the reference carrier 108 to the carrier receiving region 110, as shown in FIG. 3A.

In another embodiment, the elastic component 302 alternatively includes a tension spring. With this embodiment, installing the sample carrier 104 stretches the spring, transitioning the spring from a non-tension state to a tension state, and removing the sample carrier 104 allows the elastic component 302 to return to the non-tension state, positioning the reference carrier 108 to the carrier receiving region 110.

In another embodiment, multiple springs are utilized, including multiple compression springs and/or multiple tension springs, are employed to position the reference carrier 108 in and out of the carrier receiving region 110.

In other embodiments, one or more other elastic components (e.g., an elastomer such as rubber, a stretchable fabric, etc.) are employed to position the reference carrier 108 in and out of the carrier receiving region 110.

Figure 4A:
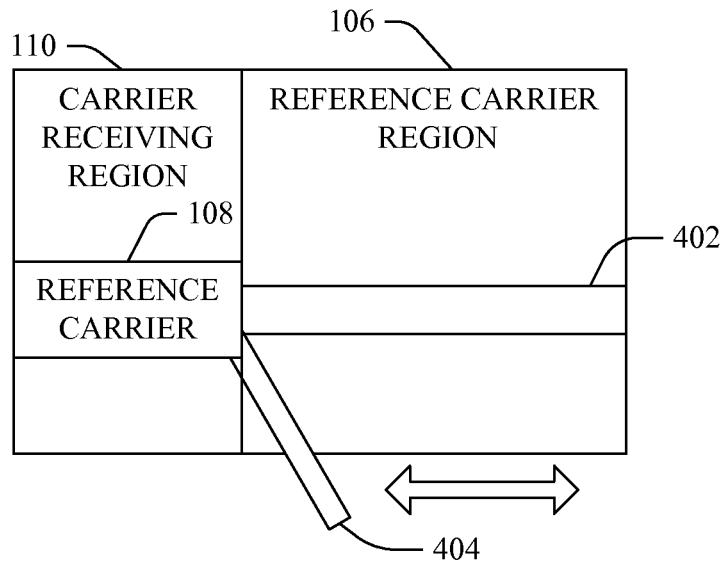
Figure 4B:
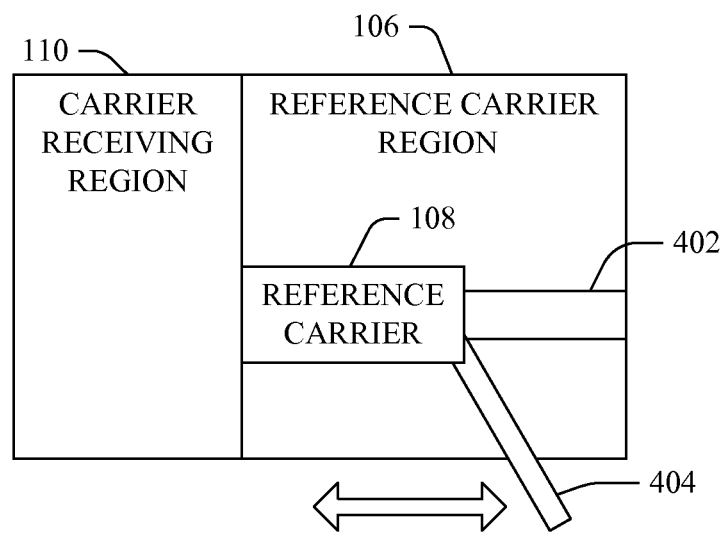

FIGS. 4A and 4B illustrate an embodiment in which the reference carrier 108 is manually moved via interaction by a user in and out of the reference carrier region 106. In both figures, the reference carrier region 106 is moveably affixed to and can slide along a track 402 via bearings or the like.

A mechanical arm 404 is affixed to an end region of the reference carrier 108. The mechanical arm 404 protrudes out of the reference carrier region 106 and the apparatus 102, and is accessible to a user of the apparatus 100. The mechanical arm 404 allows the user to slide the reference carrier 108 into the carrier receiving region 110 (FIG. 4A) and out of the carrier receiving region 110 (FIG. 4B).

Figure 5A:
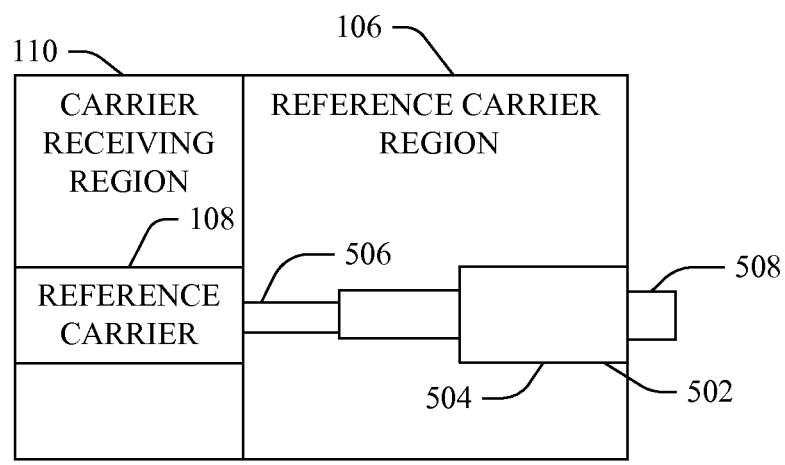
Figure 5B:
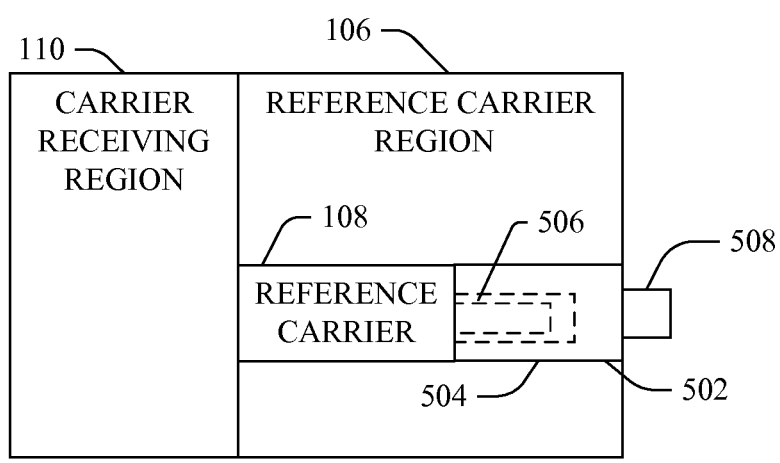

FIGS. 5A and 5B illustrate an embodiment in which the reference carrier 108 is electronically moved in and out of the reference carrier region 106. In both figures, a base end 502 of an electronically controlled telescoping device 504 is stationarily affixed to the reference carrier region 106 and a telescoping end 506 of the electronically controlled telescoping device 504 is affixed to the reference carrier 108.

A controller 508 (such as the controller 122) controls the electronically controlled telescoping device 504. For loading the reference carrier 108 into the carrier receiving region 110, the controller 508 extends the telescoping end 506 (FIG. 5A). For unloading the reference carrier 108 from the carrier receiving region 110, the controller 508 collapses the telescoping end 506 (FIG. 5B).

Optionally, one or more transducers or the like can be used to detect whether the sample carrier 104 is loaded in the carrier receiving region 110. One or more transducers or the like can additionally or alternatively be used to detect whether the reference carrier 108 is in the carrier receiving region 110 or the reference carrier region 106. The results can be provided to one or more of the controller 122 or the analyzer 120, which may invoke the controller 122 and/or the analyzer 120 to perform various actions, such as, but not limited to, running a calibration check, processing sample, etc.

In other embodiments, components such as lead screws, belts, gears, pneumatics, electromagnets, or the like can be additionally or alternatively used to move the reference carrier 108 into and out of the carrier receiving region 110.

In another embodiment, the sample carrier 104 is loaded by placing the sample carrier 104 between processing stations 112 and the reference carrier 108. In yet another embodiment, the reference carrier 108 is removed from the apparatus before loading the sample carrier 104 into the carrier receiving region 110.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A sample processing apparatus, comprising:
   a reference carrier region that supports a reference carrier, which includes one or more reference substances that emit radiation with unique and known spectral characteristics in response to being irradiated with radiation having a wavelength in a predetermined range of interest;
   a carrier receiving region configured to alternatively receive a sample carrier or the reference carrier for processing by the apparatus; and
   an optical component that emits radiation, having a wavelength in a predetermined range of interest, that irradiates the carrier in the carrier receiving region, and that detects the radiation emitted from the carrier,
   wherein the apparatus moves the reference carrier from the reference carrier region to the carrier receiving region for processing by the apparatus, and
   wherein the apparatus includes a DNA sequencer.

2. The apparatus of claim 1, wherein the optical component illuminates the reference carrier when the reference carrier is in the carrier receiving region and detects radiation emitted by the references substances thereon in response to the reference substances being illuminated, and further comprising:
   an analyzer that determines whether the apparatus is calibrated based on the detected radiation and generates a signal indicative thereof.

3. The apparatus of claim 2, wherein the optical component illuminates the reference carrier and detects the radiation and the analyzer determines whether the apparatus is calibrated at least once prior to loading a sample carrier into the carrier receiving region.

4. The apparatus of claim 2, wherein the optical component illuminates the reference carrier and detects the radiation and the analyzer determines whether the apparatus is calibrated at least once between removal of a processed sample carrier from the carrier receiving region and loading of a subsequent sample carrier into the carrier receiving region.

5. The apparatus of claim 2, wherein the optical component illuminates the reference carrier and detects the radiation and the analyzer determines whether the apparatus is calibrated during a warm up phase of the apparatus.

6. The apparatus of claim 2, wherein the apparatus recalibrates the optical component when the signal indicates that the apparatus is not calibrated.

7. The apparatus of claim 2, further comprising:
   a controller that presents a notification that indicates whether the apparatus is calibrated.

8. The apparatus of claim 1, wherein loading a sample carrier into the carrier receiving region moves the reference carrier from the carrier receiving region to the reference carrier region.

9. The apparatus of claim 8, wherein the sample carrier physically contacts and urges the reference carrier out of the carrier receiving region and into the reference carrier region.

10. The apparatus of claim 1, wherein the apparatus automatically moves the reference carrier into the carrier receiving region when a sample carrier is not loaded in the carrier receiving region.

11. The apparatus of claim 10, further comprising:
    an elastic component affixed to the reference carrier and the apparatus, wherein the elastic component is in one of a compressed or tension state when the reference carrier is in the reference carrier region and transitions to a non-compressed or non-tension as the sample carrier is unloaded from the carrier receiving region, which positions the reference carrier in the carrier receiving region.

12. The apparatus of claim 1, wherein the reference carrier region supports the reference carrier while the apparatus processes a sample carrier loaded in the carrier receiving region.

13. The apparatus of claim 1, wherein the apparatus is field deployable, and the apparatus carries the reference carrier during transportation of the apparatus to a site of deployment.

14. A method, comprising:
moving a reference carrier supported by a sample processing apparatus into a carrier receiving region of the apparatus, wherein the apparatus includes a DNA sequencer, for processing of one or more reference substances of the reference carrier by the apparatus when a sample carrier is not in the carrier receiving region, wherein the apparatus automatically moves the reference carrier into the carrier receiving region;
processing, via a processing station of the apparatus, the one or more substances carried by the reference carrier in the carrier receiving region; and
generating a signal indicating whether the apparatus is calibrated based on a result of the processing.

15. The method of claim 14, wherein the one or more reference substances emit radiation with unique and known spectral characteristics in response to be irradiated with radiation having a wavelength in a predetermined range of interest, and further comprising:
illuminating the one or more reference with radiation having the wavelength in the predetermined range of interest;
detecting the radiation emitted by the one or more reference substances in response to being irradiated with the radiation having the wavelength in the predetermined range of interest; and
determining whether the apparatus is calibrated based on the detected radiation, wherein the generated signal is indicative of the detected radiation.

16. The method of claim 15, further comprising:
comparing a spectral characteristic of the detected radiation with a predetermined spectral characteristic range for a calibrated apparatus, wherein the generated signal indicates the apparatus is calibrated in response to the spectral characteristic of the detected radiation being within the predetermined spectral characteristic range.

17. The method of claim 16, wherein the generated signal indicates the apparatus is out of calibration in response to the spectral characteristic of the detected radiation being outside of the predetermined spectral characteristic range.

18. The method of claim 15, further comprising:
automatically, via the apparatus, re-calibrating the apparatus when the signal indicates that the apparatus is out of calibration.

19. The method of claim 15, further comprising:
processing the one or more substances and generating the signal one or more times prior to processing a sample carrier loaded in the carrier receiving region.

20. The method of claim 19, wherein the one or more substances are processed during an initial phase of an executing sample carrier processing procedure.

21. The method of claim 19, wherein loading the sample carrier in the carrier receiving region automatically moves the reference carrier from the carrier receiving region to a reference carrier region of the apparatus.

22. The method of claim 21, wherein unloading the sample carrier from the carrier receiving region automatically moves the reference carrier from the reference carrier region into the carrier receiving region.

23. The method of claim 15, further comprising:
electronically moving the reference carrier between the carrier receiving region and the reference carrier region.

24. A sample processing apparatus, comprising: a component that automatically moves a reference carrier of the sample processing apparatus into a carrier receiving region of the sample processing apparatus for processing by the sample processing apparatus, wherein processing the reference carrier includes generating a signal indicative of whether the sample processing apparatus is calibrated based on optical characteristics of one or more reference substances carried by the reference carrier, wherein the sample processing apparatus includes a DNA sequencer.

* * * * *